US010126199B2

(12) United States Patent
Reedy et al.

(10) Patent No.: US 10,126,199 B2
(45) Date of Patent: *Nov. 13, 2018

(54) DETERMINING DISPLACEMENT FROM AIR FILTRATION MEDIA

(71) Applicant: K&N Engineering, Inc., Riverside, CA (US)

(72) Inventors: John Reedy, Pomona, CA (US); Steve Rogers, Murrieta, CA (US); Richard Dwyer, Arrowbear, CA (US)

(73) Assignee: K&N Engineering, Inc., Riverside, CA (US)

(*) Notice: Subject to any disclaimer, the term of this patent is extended or adjusted under 35 U.S.C. 154(b) by 101 days.

This patent is subject to a terminal disclaimer.

(21) Appl. No.: 14/300,951

(22) Filed: Jun. 10, 2014

(65) Prior Publication Data

US 2014/0290345 A1 Oct. 2, 2014

Related U.S. Application Data

(60) Continuation of application No. 13/795,226, filed on Mar. 12, 2013, now Pat. No. 8,783,092, which is a
(Continued)

(51) Int. Cl.
*G01M 3/02* (2006.01)
*B60H 1/00* (2006.01)
(Continued)

(52) U.S. Cl.
CPC .......... *G01M 3/02* (2013.01); *B60H 1/00585* (2013.01); *B60H 3/0633* (2013.01);
(Continued)

(58) Field of Classification Search
CPC .......... G01N 2015/084; B01D 46/0086; B01D 2273/18; B01D 35/143; G01M 3/02; G01M 3/025
(Continued)

(56) References Cited

U.S. PATENT DOCUMENTS 4,235,098 A 11/1980 Tisch
4,875,360 A * 10/1989 Ziemer .................. G01M 3/20
73/38
(Continued)

FOREIGN PATENT DOCUMENTS

DE 10011940 A1 * 9/2001 ......... G01N 15/0826

OTHER PUBLICATIONS

Machine translation of DE 10011940 A1.*

*Primary Examiner* — Peter Macchiarolo
*Assistant Examiner* — Nathaniel Kolb
(74) *Attorney, Agent, or Firm* — Rutan & Tucker LLP; Hani Z. Sayed

(57) ABSTRACT

An apparatus and a system is provided that may be utilized to determine oil migration and oil displacement from a pre-oiled air filter. The present invention may also be utilized to determine if oil is displaced from the air filter onto a portion of the apparatus for visualization to a user. The present invention utilizes a demonstration apparatus having a system for forcing air through the oil subjected air filter thereby attempting to force displacement of the oil from the air filter. The apparatus utilizes a blowing means whereby the oil infused air filter is subject to higher than normal air flow and whereby the apparatus has a deflection portion whereby if oil is displaced from the air filter, it is deflected onto the deflection portion where it would be physically viewable to an observer present in the vicinity of the apparatus.

10 Claims, 3 Drawing Sheets

Related U.S. Application Data continuation of application No. 13/192,736, filed on Jul. 28, 2011, now Pat. No. 8,418,528, which is a continuation of application No. 12/617,586, filed on Nov. 12, 2009, now Pat. No. 8,028,564, which is a division of application No. 11/837,445, filed on Aug. 10, 2007, now Pat. No. 7,637,146.

(51) Int. Cl.
  *B60H 3/06* (2006.01)
  *G01N 15/08* (2006.01)
  *G01N 11/00* (2006.01)

(52) U.S. Cl.
  CPC .......... *B01D 2273/18* (2013.01); *G01N 11/00* (2013.01); *G01N 2015/084* (2013.01)

(58) Field of Classification Search
  USPC ........................................ 73/37, 49.7, 865.9
  See application file for complete search history.

(56) References Cited

U.S. PATENT DOCUMENTS

| | | | |
|---|---|---|---|
| 6,680,028 B1 | 1/2004 | Harris | |
| 7,637,146 B2* | 12/2009 | Reedy | B60H 1/00585 73/38 |
| 8,028,564 B2* | 10/2011 | Reedy | B60H 1/00585 73/38 |
| 8,418,528 B2* | 4/2013 | Reedy | B60H 1/00585 73/38 |
| 8,783,092 B2* | 7/2014 | Reedy | B60H 1/00585 73/38 |
| 2009/0038377 A1* | 2/2009 | Reedy | B60H 1/00585 73/40.5 R |
| 2010/0050878 A1* | 3/2010 | Reedy | B60H 1/00585 96/188 |
| 2011/0277641 A1* | 11/2011 | Reedy | B60H 1/00585 96/415 |
| 2013/0192347 A1* | 8/2013 | Reedy | B60H 1/00585 73/49.7 |

* cited by examiner

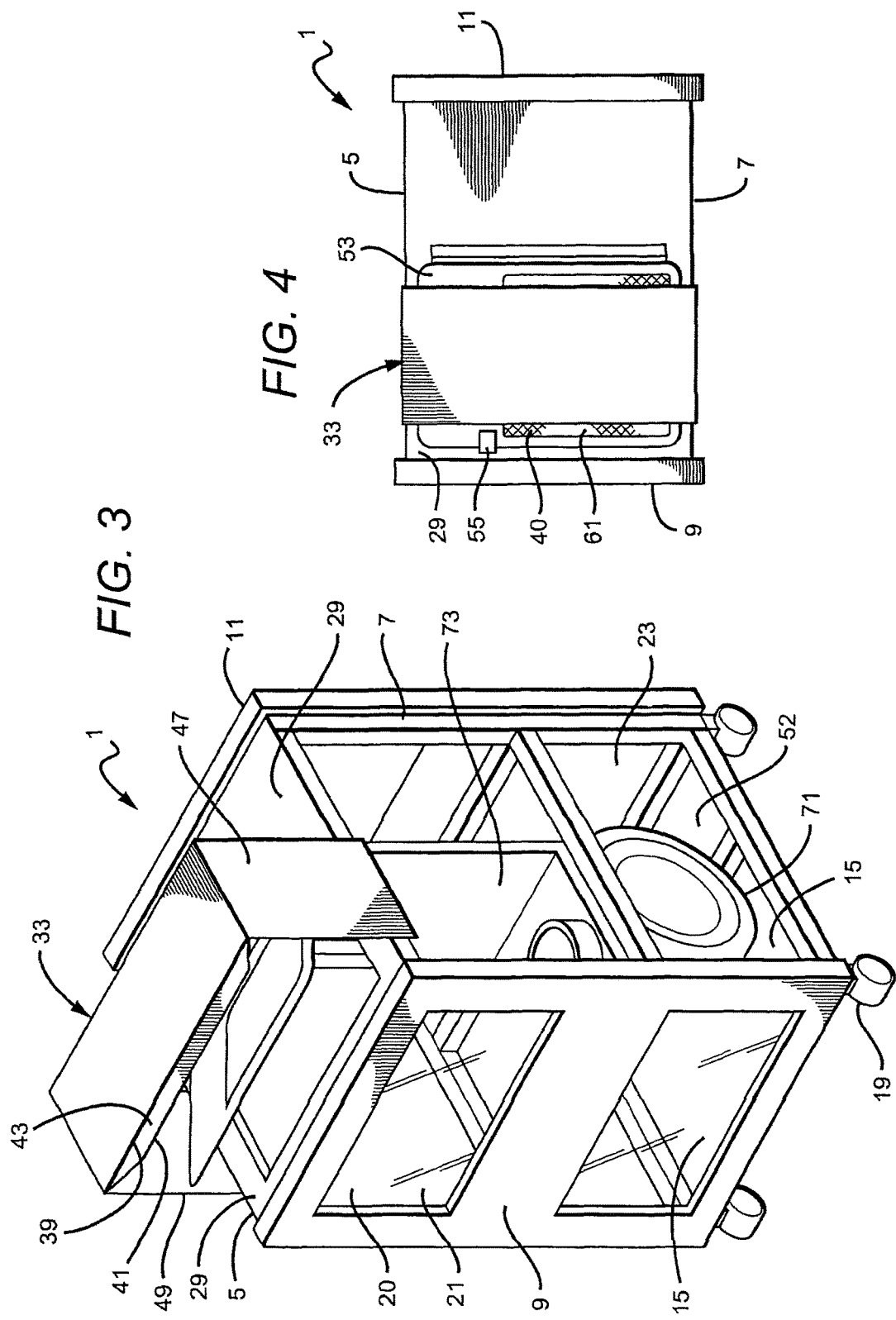

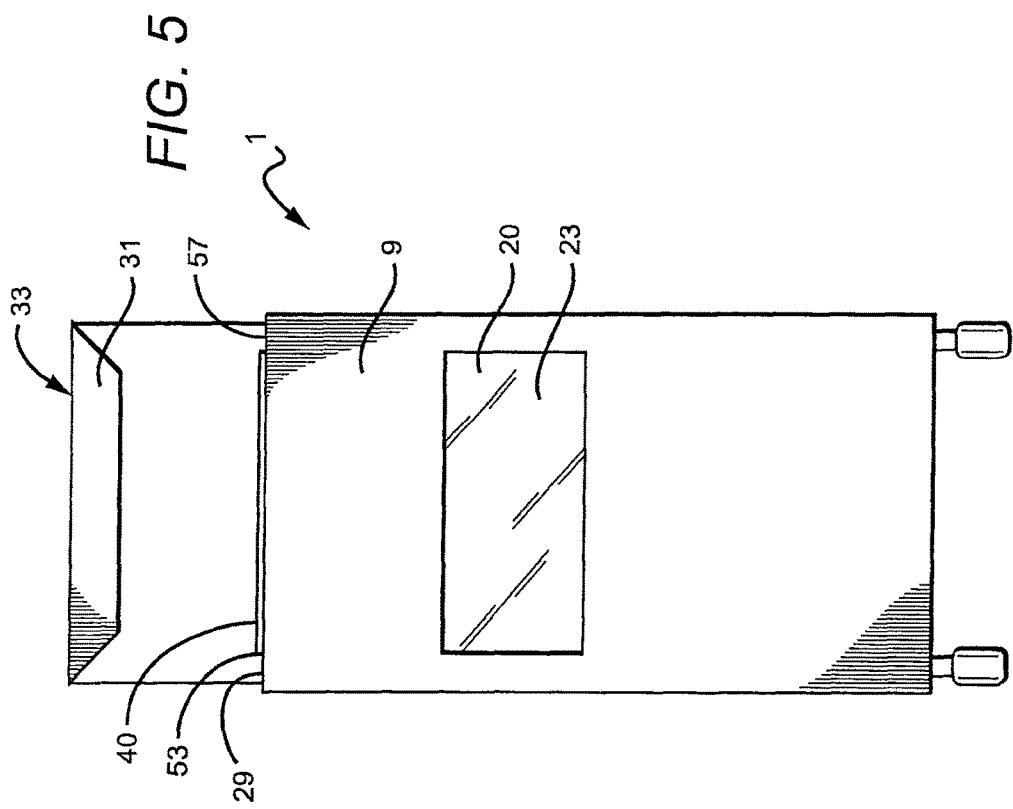

DETERMINING DISPLACEMENT FROM AIR FILTRATION MEDIA

CROSS-REFERENCE TO RELATED APPLICATION

This application is related to and claims priority from U.S. patent application Ser. No. 13/795,226 filed on Mar. 12, 2013, U.S. patent application Ser. No. 13/192,736 filed on Jul. 28, 2011, now U.S. Pat. No. 8,418,528, which is a continuation of U.S. patent application Ser. No. 12/617,586 filed on Nov. 12, 2009, now U.S. Pat. No. 8,028,564 issued Oct. 4, 2011, which is a division of U.S. application Ser. No. 11/837,445 filed on Aug. 10, 2007, now U.S. Pat. No. 7,637,146 issued Dec. 29, 2009.

FIELD OF THE INVENTION

The present invention relates generally to the field of vehicle performance parts. More specifically, the present invention relates to apparatus and system to determine oil migration away from a vehicle air filter.

BACKGROUND OF THE INVENTION

On any given vehicle, there are thousands of functioning and necessary parts to make the vehicle move. These essential parts are usually interlinked with other parts as part of an overall system to make the vehicle run efficiently.

For many car enthusiasts, modifying a factory vehicle with upgraded aftermarket parts is rewarding and satisfying in a multiplicity of different ways. Many individuals decide to modify their vehicles for aesthetic purposes. However, many individuals modify or alter their vehicles to elicit better performance from their vehicle or to upgrade from more restrictive parts that come with their vehicle from the factory to less restrictive parts with better usability and/or performance.

There are some very common aftermarket modifications that most vehicle enthusiasts, such as car owners, motorcycle owners, boat, and other gasoline/diesel powered vehicle owners choose to employ. A few of these common aftermarket modifications are replacement of a vehicle exhaust system, and replacement of headers (which are tubes that run from the engine and direct unwanted heat and exhaust away from the engine). Additionally, many individuals will recalibrate a vehicle's computer which regulates engine speed and other functions, to elicit higher performance and tolerances. However, the most common type of vehicle modification is the replacement of the stock air filter with an aftermarket type air filter.

The two main types of air filters that are used in vehicles are the combustion air filter, and the cabin air filter. The cabin air filter is a pleated paper filter that is placed in the outside-air intake for the vehicle's passenger compartment. Some of these filters are rectangular and similar in shape to the combustion air filter. Others are uniquely shaped to fit the available space of a particular vehicle's outside-air intake. This type of filter is relatively new to the car industry and often gets clogged and dirty. Newer cabin air filters may reduce allergens and may utilize additional compositions to reduce particulates, odors and the like.

Combustion air filters are used in vehicles to prevent abrasive particulate matter from entering the engine. If particulate matter enters the engine, it could cause mechanical problems or contamination of vital fluids needed for proper engine management, including contamination of engine oil.

Most modern, fuel injected vehicles use some sort of pleated paper filter element in the form of a flat panel. This filter is usually placed inside a plastic box connected to the throttle body with a large hose. The filter may stop particulate matter and other contaminates from entering the engine and causing damage or degradation of the engine.

Most air filters are constructed from similar materials. Traditional prior art air filters are constructed from a pleated paper filter because they are efficient, easy to use and cost-effective. Other air filters are constructed of different materials such as cotton, foam and the like. Aftermarket filters are typically constructed of one and/or a combination of these materials and may allow for more air flow from the outside of the vehicle to the engine, which may increase engine performance while still reducing contaminant intrusion into the engine.

A very large aftermarket presence has arisen from the replacement of the stock factory air filter with a newer, more efficient filter that may allow for increased air flow through the filter and subsequently into the engine. A pioneer in the replacement air filter is the company K&N® Engineering, Inc. K&N® developed a new air filter which is composed of a cotton gauze material which is placed between aluminum wire mesh. The new air filter was the first of its kind that was not constructed to be replaced after a period of time. The K&N® filter was made to withstand repeated washing of the filter, while still operating effectively as a tool to filter particulates. In order for the K&N® filter to operate effectively in filtering particulates, dust and a plurality of other particles, the filter is treated with a specially formulated oil. When the filter is accessed, and subsequently washed, the filter needs to be oiled to attract and retain particulates once it is re-inserted into the vehicle. This specially formulated oil is applied to the filter after the filter has been cleaned and prior to insertion into the vehicle.

However, one problem that exists, is that many individuals believe that this oil is harmful to the rest of the vehicle once applied to the air filter. Many individuals are under the misconception that the oil that is applied to the air filter may find its way into the throttle body of the engine and ultimately into the engine itself. Additionally, another problem that exists, is that many individuals believe that the oil migrates off the air filter and may affect other engine and vehicle systems including mass air sensors and other delicate vehicle sensors that should be kept unobstructed from liquid application thereto.

A need therefore exists for an apparatus and system to determine if the oil applied to an air filter does in fact migrate on the air filter and/or away from the same. Additionally, a need therefore exists for an apparatus and system that may be utilized to determine if oil migrates off the air filter or may be projected away therefrom.

Moreover, a need exists for a system that may illustrate the possible migration of oil from the air filter to a viewer to determine if migration of oil does occur from the filter itself.

SUMMARY OF THE INVENTION

The present invention relates to an apparatus and a system that may be utilized to determine oil migration on and/or away from an air filter. The present invention may also be utilized to determine if oil is displaced from the air filter onto a portion of the apparatus for visualization to a user/viewer. The present invention utilizes a demonstration apparatus having a system for forcing air through the oil-treated air filter thereby forcing possible displacement of the oil from the air filter. The apparatus utilizes a blowing means whereby the oil infused air filter is subject to higher than normal air flow and whereby the apparatus has a deflection portion whereby if oil is displaced from the air filter, it is projected onto the deflection portion where it would be physically viewable to an observer present in the vicinity of the apparatus.

To this end, in an exemplary embodiment of the present invention, an apparatus for determining displacement from a filtration media is provided. The apparatus has a container means having at least a side, and a top and bottom portion. Additionally, the apparatus has an accommodation portion whereby the accommodation portion has an opening thereon for accommodating an air filtration media. Moreover, the apparatus has a blower means for directing air flow through the air filtration media. Further, the apparatus has an extension receptacle positioned above the air filtration media.

In an exemplary embodiment, the apparatus has an accommodation portion wherein the accommodation portion holds an air filter or air filtration media.

In an exemplary embodiment, the apparatus has a channel connecting the blower means to the accommodation portion whereby the blower means directs forced air into the accommodation portion and through the air filtration media.

In an exemplary embodiment, the apparatus has an extension receptacle wherein the extension receptacle is positioned above the air filtration media and further wherein the extension receptacle has a top portion, a bottom portion and two side portions.

In an exemplary embodiment, the apparatus has an extension receptacle wherein the extension receptacle positioned above the air filtration media has a top portion, a bottom portion and two side portions whereby a wedge is formed between the two side portions and further wherein said wedge extends downwards from the bottom portion of the extension receptacle.

In an exemplary embodiment, the apparatus accommodates an air filtration media wherein the air filtration media is a vehicle air filter.

In an exemplary embodiment, the apparatus has a container means wherein the container means has at least one transparent portion whereby a viewer may observe the interior portion of the container means.

In an exemplary embodiment, the apparatus has an extension receptacle being constructed of white powder coated aluminum to facilitate observation of any non white particles displaced thereto.

In an exemplary embodiment, the apparatus has a container means wherein the front portion, top portion, and side portions of the container means are constructed of clear plexi-glass.

In an exemplary embodiment, the apparatus has an extension receptacle wherein the extension receptacle is constructed of a light colored material whereby any displaced byproducts will be observable to a viewer.

In an exemplary embodiment, the apparatus has an extension receptacle wherein the extension receptacle has a wedge extending downwardly away from a bottom portion of the receptacle to be in closer proximity with the air filtration media whereby if any particle and/or oil is displaced from the air filtration media, it will be attracted and adhered to the wedge of the extension receptacle.

In an exemplary embodiment, the apparatus has a blower means wherein the blower means is any device capable of forcing air through an air filtration media.

To this end, in an exemplary embodiment of the present invention, a system for determining displacement from a filtration media is provided. The system has a container means having an accommodation portion whereby the accommodation portion has an opening thereon for accommodating an air filtration media. Additionally, the system has a blower means for directing air through the air filtration media. Further, the system has an extension portion positioned above the air filtration media.

In an exemplary embodiment, the system has an extension portion wherein the extension portion positioned above the air filtration media extends above the air filtration media and covers the entire width and length of the air filtration media.

In an exemplary embodiment, the system has an extension portion wherein the extension portion positioned above the air filtration media is adapted to accept and display any displaced particulate from the air filtration media.

In an exemplary embodiment, the system has an extension portion wherein the extension portion has a wedge shaped portion extending downwardly from the bottom of the extension portion to be in close proximity to the air filtration media.

In an exemplary embodiment, the system has an accommodation portion wherein the accommodation portion may be constructed to fit a plurality of different air filtration media.

In an exemplary embodiment, the system has a blower means wherein the blower means is a blower capable of forcing air through the air filtration media at a rate greater than two times the normal operating air flow of the air filtration media's normal vehicle operating air velocity.

To this end, in an exemplary embodiment of the present invention, an apparatus and system for measuring oil migration from an air filter is provided.

In another exemplary embodiment, an apparatus and a system for measuring and observation of possible oil migration is provided. The apparatus may be utilized for illustrative purposes.

Another exemplary embodiment is an apparatus and system for measuring and observing oil migration whereby air may be forced through an air filter in an attempt to displace the specially formulated oil treatment from the air filter.

Yet another exemplary embodiment of the present invention is to provide an apparatus and a system for observing air flow through an oil infused filter media.

Still another exemplary embodiment of the present invention is to provide an apparatus and a system for observing air flow and potential displacement of oil from an air filter media.

An exemplary embodiment of the present invention is to provide an apparatus and a system for observing air flow through an oiled filter media whereby the air velocity of the air flow through a filter does not displace the oil from the air filter media.

Yet another exemplary embodiment of the present invention is to provide an apparatus and a system for observing oil migration or lack thereof off an air filter whereby the apparatus has a display means to display the results of any potential oil migration therefrom.

Another exemplary embodiment of the present invention is to provide an apparatus and a system whereby the apparatus may use a high pressure blower means whereby the blower means may force higher than normal air velocities through the air filter in an attempt to displace the oil contained therein.

Still another exemplary embodiment of the present invention is to provide an apparatus and a system for observation of oil migration from an air filter media whereby the apparatus may have a blower means whereby the blower means may increase the normal air velocity through an air filter by at least three times that of the normal operating conditions found in a typical vehicle.

Yet another exemplary embodiment of the present invention is to provide an apparatus and a system for observation of oil migration of an air filter media to the surrounding environment to determine if oil is displaced from its position on the air filter media.

Still another exemplary embodiment of the present invention is to provide an apparatus and a system for observation of possible oil migration from an air filter media wherein the apparatus may have a display portion whereby the display portion is positioned directly within the zone of air flow exiting the air filter media.

Another exemplary embodiment of the present invention is to provide an apparatus and a system for observation of possible oil migration from an air filter media wherein the apparatus may have a display portion whereby the display portion is positioned directly within the zone of air flow exiting the air filter media and whereby if oil is projected off of the air filter media, it will be physically visible on the display portion.

An exemplary embodiment of the present invention is to provide an apparatus and a system for observation of possible oil migration from an air filter media wherein the apparatus may have a display portion whereby the display portion is positioned directly within the zone of air flow exiting the air filter media whereby the display portion is constructed of a material that will display any projected oil leaving the filter.

Still another exemplary embodiment of the present invention is to provide an apparatus and a system for observation of possible oil migration from an air filter media wherein the apparatus may have a display portion whereby the display portion is positioned directly within the zone of air flow exiting the air filter media whereby the display portion may be shaped in such a way to capture oil escaping from the filter.

Yet another exemplary embodiment of the present invention is to provide an apparatus and a system for observation of oil migration from an air filter media wherein the apparatus may have a display portion whereby the display portion is positioned in the direction of the exiting air flow from the second side of an air filter media whereby the display portion may be constructed in a contrasting color to illustrate oil that may be displaced from the air filter onto the display portion.

Still another exemplary embodiment of the present invention is to provide an apparatus and a system for observation of oil migration from an air filter media whereby the apparatus may have a top portion whereby the top portion has an opening thereon for insertion of an air filter.

Another exemplary embodiment of the present invention is to provide an apparatus and a system for observation of oil migration from an air filter media whereby the apparatus may have a top portion adapted for insertion of an air filter whereby above the air filter insertion portion is the display means.

Yet another exemplary embodiment of the present invention is to provide an apparatus and a system for observation of oil migration from an air filter media wherein the apparatus may have a transparent portion for an observer to view the air flow through the air filter.

Still another exemplary embodiment of the present invention is to provide an apparatus and a system for observation of oil migration from an air filter media wherein the apparatus may be utilized to observe oil migration through an air filter that may be utilized in a vehicle such as a car, motorcycle, ATV, truck, boat, personal watercraft and the like.

Another exemplary embodiment of the present invention is to provide an apparatus and a system for observation of oil migration through an air filter media which may be utilized to determine if oil escapes from the air filter at different air velocities.

Yet another exemplary embodiment of the present invention is to provide an apparatus and a system for observation of oil migration from an air filter media whereby the apparatus may be monitored with the use of a wedge that covers the entire length and width of the air filter media, and will attract and detain any particulate displaced from the air filter media.

Still another exemplary embodiment of the present invention is to provide an apparatus and a system for observation of oil migration from an air filter media whereby the apparatus may be monitored with a display portion that covers the entire length and width of the air filter media.

Still another exemplary embodiment of the present invention is to provide an apparatus and a system for observation of oil migration from an air filter media whereby the apparatus may discharge much higher air velocities than a normal air filter in a vehicle is subjected to.

Yet another exemplary embodiment of the present invention is to provide an apparatus and a system for observation of oil migration from an air filter media whereby the apparatus may have a wedge mounted above the air filter in the discharge air stream wherein the wedge has a bright surface that will show deposits of oil if exposed thereto.

In yet another exemplary embodiment of the present invention is to provide an apparatus and a system for observation of oil migration from an air filter media whereby the apparatus may have a means for measuring and monitoring the velocity of the air discharge with a wind velocity meter.

Another exemplary embodiment of the present invention is to provide an apparatus and a system for observation of oil migration from an air filter media whereby the apparatus may have a means for measuring and monitoring the velocity of the air discharge from the air filter in miles per hour.

Still another exemplary embodiment of the present invention is to provide an apparatus and a system for observation of oil migration from an air filter media whereby the apparatus may have a means for measuring and monitoring the velocity of the air discharge from the air filter in kilometers per hour.

Yet another exemplary embodiment of the present invention is to provide an apparatus and a system for observation of oil migration from an air filter media whereby the apparatus may have a means for measuring and monitoring the velocity of the air discharge from the air filter in knots.

Another exemplary embodiment of the present invention is to provide an apparatus and a system for observation of oil migration from an air filter whereby the apparatus may illustrate an air filter media's lack of migration of oil from the media even under the most severe operating conditions.

Various objects, features, aspects and advantages of the present invention will become more apparent from the following detailed description of preferred embodiments of the invention, along with the accompanying drawings in which like numerals represent like components.

Additional features and advantages of the present invention are described herein, and will be apparent from the detailed description of the presently preferred embodiments and from the drawings.

BRIEF DESCRIPTION OF THE DRAWING

FIG. 3 is perspective view of the apparatus in an exemplary embodiment of the present invention;

FIG. 4 is a top view of the apparatus in an exemplary embodiment of the present invention;

FIG. 5 is a back view of the apparatus in an exemplary embodiment of the present invention; and FIG. 6 is side perspective view of the apparatus illustrating the wedge shaped display means in an exemplary embodiment of the present invention.

DETAILED DESCRIPTION

Figure 1:
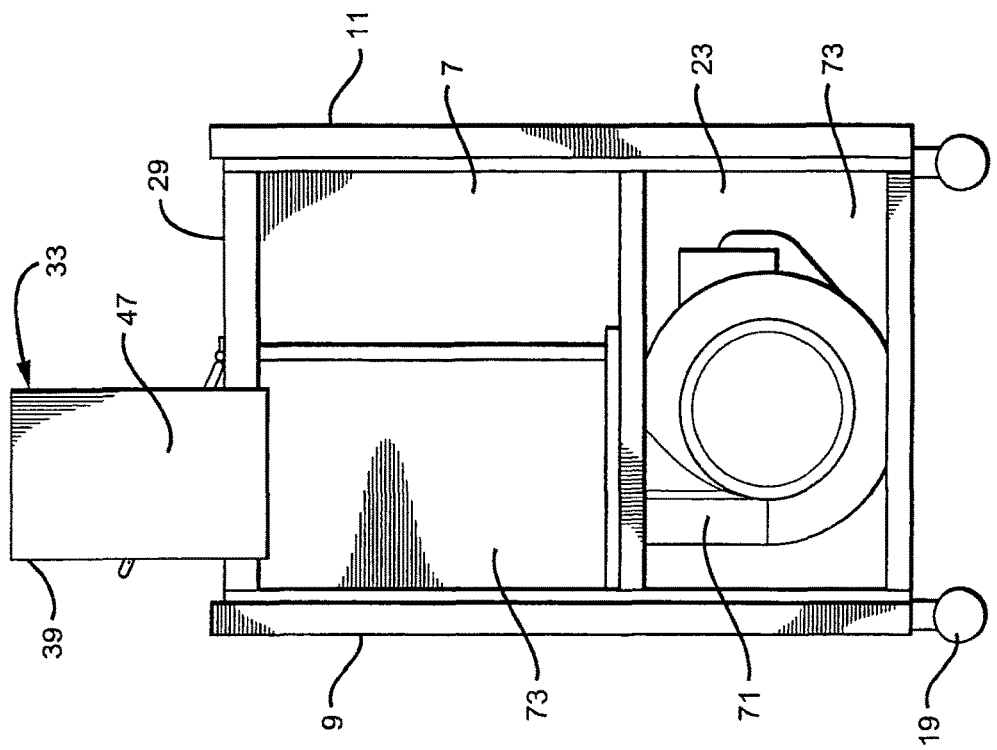
FIG. 1 is a front perspective view of the apparatus in an exemplary embodiment of the present invention.

Turning now to the drawings wherein elements are identified by numbers and like elements are identified by like numbers throughout the 6 figures, the invention is depicted in FIG. 1 and illustrates an oil migration apparatus that may be utilized to illustrate the possibility of oil migration from an air filtration media.

Referring first to FIG. 1, an oil migration apparatus 1 is provided. The oil migration apparatus 1 (hereinafter referred to as a device) may have a plurality of different configurations, but for illustrative purposes is shown in only a single embodiment for ease of description. Thereby, the device 1 may have a first side 5 and a second side 7. Additionally, the device 1 may have a front portion 9 and a rear portion 11. Moreover, the device 1 may further have a top portion 29 and a bottom portion 15. The device may also have wheels 19 attached to the bottom portion 15 of the device 1 for movement and relocation of the device 1 when desired for illustrative purposes. The wheels 19 may allow the device 1 to be moved from one location to another where the device 1 may be used, installed and utilized for illustration to a plurality of different viewers (not shown).

As further illustrated in FIG. 1, the oil migration apparatus 1 may a viewable portion 21 in the front portion 9 of the device 1. In an exemplary embodiment, this viewable portion 21 may be constructed of plexi-glass 20. However, it should be understood that the viewable portion 21 may be constructed of any suitable transparent material that would allow the viewer to view the interior portion 23 of the container 25. Therefore, the viewable portion 21 may be constructed of glass, plastic, or any other transparent material. The preferred embodiment contemplates having this viewable portion 21 located at the top 29 of the front portion 9. However, the viewable portion 21 may encompass the entirety of the front portion 9. It should also be understood that the viewable portion 21 may be contained on the first side 5 and on the second side 7, and/or may be positioned on the back portion 11 of the device 1 for illustration of the interior portion 23 of the oil migration apparatus 1 to the viewer.

FIG. 1 further illustrates the top portion 29 of the oil migration device 1 whereby the top portion 29 has a wedge 31 and the wedge 31 is attached to an extension portion 33. The extension portion 33 extends away from the top portion 29 of the device 1 and is situated above the top portion 29.

The wedge 31 may be configured to attach to a first side 5 of the extension portion 33 and a second side 7 of the extension portion 33. The wedge 31 may extend down from the bottom side 39 of the extension portion 33 whereby the apex 41 of the wedge 31 is closer in proximity to an air filtration media 40. A first edge 43 of the wedge 31 extends away from the apex 41 and towards the bottom side 39 of the extension portion 33. Similarly, the second edge 45 of the wedge 31 extends away from the apex 41 towards the bottom side 39 of the extension portion 33. The first and second edges 43, 45 of the wedge 31 form linear planes that are in an exemplary embodiment painted a bright color to illustrate if any particulates are displaced onto the linear edges 43, 45 for illustration to a user and/or observer.

Additionally, as illustrated in FIG. 1, the extension portion 33 may have a first arm 47 and a second arm 49 that attaches the extension portion to the top portion 29 of the oil migration device 1. The first and second arms 47, 49 of the extension portion 33 allow for attached and removal of the extension portion 33 and allow for placement of the wedge 31 into closer proximity to the air filtration media located on the top portion 29 of the device 1.

Figure 2:
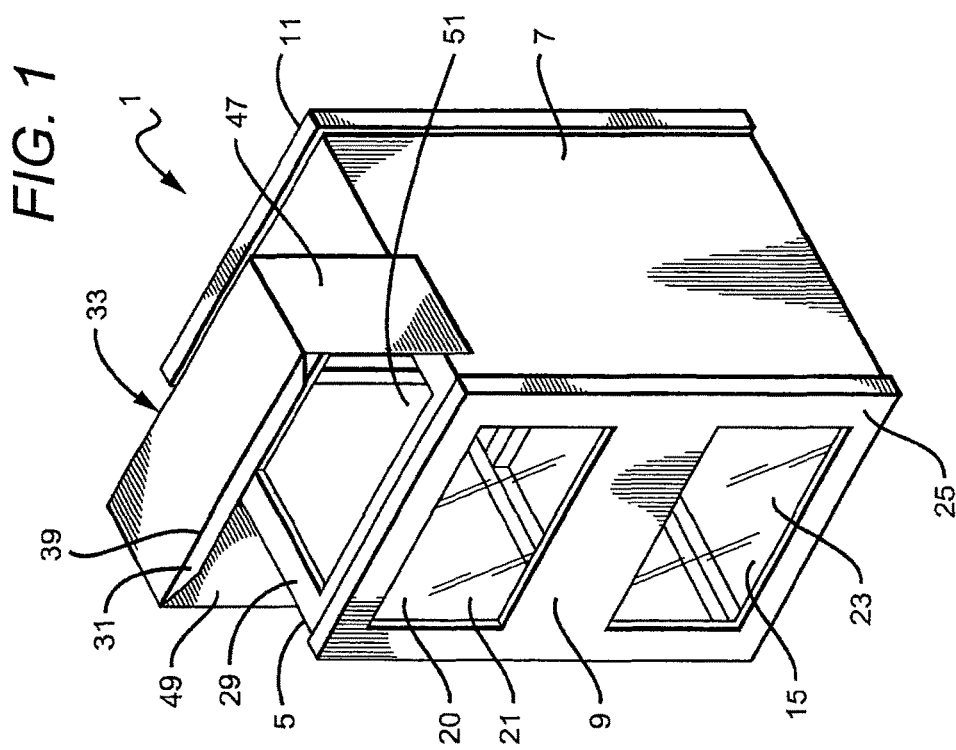
FIG. 2 is a side cross-sectional view of the apparatus in an exemplary embodiment of the present invention.

As can be seen from FIGS. 1 and 2, the device 1 may have an air filtration media 40 contained on the top portion 29 of the oil migration device 1. Although in an exemplary embodiment, the present invention illustrates the use of one filtration media 40 and an accommodation position 51 for the singular air filtration media 40, it should be understood that the device 1 is not limited to a singular air position 51 for the media 40. The invention may be utilized for any number of air filters and can have substantially more than the illustrated accommodation position 51.

Additionally, FIG. 1 illustrates the blower 71 utilized to create air velocity through the air filter 40 and to attempt to displace oil dispensed onto the air filter 40. In an exemplary embodiment, the air filtration media 40 may have a specially formulated oil 61 dispersed thereto as utilized in a plurality of different aftermarket air filtration media 40. After the oil 61 is dispensed onto the air filter 40, the air filter 40 may be placed on the top portion 29 of the device 1 whereby the air filter 40 may be subjected to a high level of air velocity and/or pressure. As illustrated in FIG. 1, the blower 71 may be positioned at the bottom section 52 of the device 1 and may direct air velocity through the air filter 40 positioned on the top portion 29 of the device 1. It is contemplated that the blower 71 may provide substantially higher air velocity than the normal air velocity experienced by a typical vehicle (not shown).

FIG. 2 illustrates a side cross section view of the oil migration device 1. As can be seen, the blower 71 may be located in the bottom portion 52 of the interior 23 of the oil migration device 1. The blower 71 air velocity may be directed towards the air filter media 40 positioned at the top portion 29 of the device 1. Additionally, FIG. 2 illustrates a channel 73 that is positioned within the interior portion 23 of the device 1 to channel the air from the blower 71 toward the air filter media 40 thereby ensuring that a sufficiently high air velocity is directed at the air filter media 40 in an attempt to force the migration and release of oil 61 from the air filter media 40.

FIG. 3 illustrates a perspective view of the oil migration device 1. As can be seen from the illustration, the first 47 and second arms 49 extend away from the top portion 29 of the device 1 and provide for an extension portion 33 housing the wedge 31. Additionally, FIG. 3 illustrates the accommodation portion 53 on the top portion 29 of the device 1 whereby the accommodation portion 53 may accommodate the insertion and removal of an air filter 40. The accommodation portion 53 may be of adequate size to accommodate a specific air filter 40 and/or may utilize an adaptor (not shown) that may allow for utilization of a plurality of different air filter media 40 having different sizes, dimensions and weights.

It should also be noted, that the air filter media 40 may be inserted and extracted from the accommodation portion 53 and another sized, dimensioned or weighted air filter having the oil 61 dispensed thereon be placed in the accommodation portion 53 to illustrate that each of a plurality of different air filter media 40 will have substantially similar results from oil migration testing.

FIG. 4 illustrates a top view of the device 1 whereby the extension portion 33 may be viewed along with the accommodation portion 53 whereby the accommodation portion 53 may be sized and dimensioned to accommodate a variety of different air filter media 40. In an exemplary embodiment, the extension portion 33 with its extended wedge 31 may be sized to entirely overlap with the accommodation portion 53 whereby if any oil 61 escapes from the air filter media 40 positioned within the accommodation portion 53, the wedge 31 and extension portion 33 are in a position to accept any transfer or displacement of oil and/or any other particulates.

Additionally, the extension portion 33 and the accommodation portion 53 may be positioned at the front portion 9 of the device 1 for ease of illustration to a user. However, it should be understood that the extension portion 33 and accommodation portion 53 may be positioned at any part of the device 1 for illustration to a viewer. In an exemplary embodiment of the present invention, a wind meter 55 may be utilized within the extension portion 33 to determine the wind velocity through the air filter media 40 to allow the viewer to determine that the pressure and velocity through the air filter media 40 is greater than normal air velocity through an air filter media 40 in a normal vehicle.

FIG. 5 illustrates a front view of the device 1 whereby a plexi-glass 20 and/or transparent covering is illustrated on the front portion 9 of the device 1. The transparent covering allows the viewer to visually observe the interior area 23 of the device, including the blower 71 and the directional channel 73 that directs air flow through the air filter media 40 on the top portion 29 of the device 1. Additionally, FIG. 5 illustrates the extension portion 33 along with the wedge 31 that encompasses a large percentage of the top area 57 of the device 1, thereby capturing any oil or particulate displacement off the air filter media 40 contained within the accommodation portion 53 of the device 1.

FIG. 6 illustrates the extension portion 33 of the device 1. As can be seen in FIG. 6, the extension portion 33 may have a first arm 47 and a second arm 49 that may be removably secured to the top portion 29 of the device 1. In an exemplary embodiment a wedge 31 may be placed thereon whereby the wedge 31 may extend in a direction away from the bottom portion 39 of the extension portion 33 and in a direction in close proximity to the air filtration media 40 positioned on the top portion 29 of the device 1, whereby if oil 61 or other particulate is displaced from the air filter media 40 as a result of high air velocity being passed through the filter 40, the wedge 31 would be in close proximity to the air filter media 40 and may capture any discharged oil 61 therefrom. In another exemplary embodiment, the wedge 31 may be substituted with a flat plane or semi-circular portion and/or any other embodiment that would allow for close proximity and accommodation of any discharged and/or displaced oil 61 from the air filter media 40 contained on the device 1. In an exemplary embodiment, the wedge 31 may be painted in a bright color to illustrate to a viewer the contrast between the paint and any oil 61 discharged from the air filter media 40.

Thus, specific embodiments and applications of a safety device system have been disclosed. It should be apparent, however, to those skilled in the art that many more modifications besides those already described are possible without departing from the inventive concepts herein. The inventive subject matter, therefore, is not to be restricted except in the spirit of the appended claims. The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An apparatus for determining oil displacement from filtration media, the apparatus comprising:
   a container means having at least a side, and a top and bottom portion;
   an accommodation portion whereby the accommodation portion wherein the accommodation portion has an opening to accommodate the filtration media;
   a blower means for directing air flow through the filtration media; and
   a transparent covering disposed on a front portion so as to allow observation of an interior area of the apparatus and the blower; and
   an extension receptacle positioned above the filtration media, the extension receptacle including a first arm and a second arm that are removably secured to the top portion, the top portion further comprising a wedge, wherein first and second edges of the wedge form linear planes configured to illustrate displaced particulates thereon.

2. The apparatus of claim 1 wherein the accommodation portion holds the filtration media.

3. A system for determining displacement from air filtration media, the system comprising:
   a container means having an accommodation portion whereby the accommodation portion has an opening thereon for accommodating the air filtration media wherein the accommodation portion has an opening to accommodate an filtration media;
   a blower means for directing air through the air filtration media; and
   a transparent covering disposed on a front portion so as to allow observation of an interior area of the system and the blower; and
   an extension portion positioned above the air filtration media, the extension portion including a first arm and a second arm that are secured to a top portion of the system, and a top portion further comprising a wedge, wherein first and second edges of the wedge form linear planes configured to illustrate displaced particulates thereon.

4. The system of claim 3 wherein the extension portion positioned above the air filtration media extends above the air filtration media and covers the entire width and length of the air filtration media.

5. The system of claim 3 wherein the extension portion positioned above the air filtration media is adapted to accept and display any displaced material from the air filtration media.

6. The system of claim 3 wherein the accommodation portion is constructed to fit a plurality of different air filtration media.

7. An apparatus for determining oil displacement from filtration media, the apparatus comprising:
- a container means having at least a side, a top and bottom portion;
- an accommodation portion whereby the accommodation portion has an opening thereon for accommodating an air filtration media wherein the accommodation portion has an opening to accommodate an filtration media;
- a blower means for directing air flow through the air filtration media; and
- a transparent covering disposed on a front portion so as to allow observation of an interior area of the apparatus and the blower;
- an extension receptacle positioned above the air filtration media wherein the extension receptacle has a wedge extending downwardly away from a bottom portion of the receptacle to be in closer contact with the air filtration media whereby if any particle is displaced from the air filtration media, it will be illustrated onto first and second edges of the wedge, the first and second edges configured as linear planes; and
- the extension portion including a first arm and a second arm that are secured to a top portion of the apparatus.

8. A system for determining displacement from a filtration media, the system comprising:
- a container means having an accommodation portion whereby the accommodation portion has an opening thereon for accommodating the air filtration media;
- a blower means for directing air through the air filtration media; and
- a transparent covering disposed on a front portion so as to allow observation of an interior area of the system and the blower;
- an extension portion positioned above the air filtration media wherein the extension portion has a wedge shaped portion extending downwardly from the bottom portion of the extension portion to be in close proximity to the air filtration media; and
- the top portion further comprising a wedge, wherein first and second edges of the wedge form linear planes configured to illustrate displaced particulates thereon.

9. The system of claim 8 wherein the extension portion positioned above the air filtration media extends above the air filtration media and covers the entire width and length of the air filtration media.

10. The system of claim 8 wherein the accommodation portion is may be constructed to fit a plurality of different air filtration media.

\* \* \* \* \*